United States Patent
Ikeda et al.

(10) Patent No.: US 8,428,338 B1
(45) Date of Patent: Apr. 23, 2013

(54) METHOD OF DETERMINING SOLDER PASTE HEIGHT AND DEVICE FOR DETERMINING SOLDER PASTE HEIGHT

(75) Inventors: Masanori Ikeda, Yamanashi (JP);
Michinori Tomomatsu, Yamanashi (JP);
Masahiro Taniguchi, Yamanashi (JP);
Yousuke Hassaku, Yamanashi (JP);
Hiroshi Okamura, Kumamoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/698,684

(22) PCT Filed: Feb. 20, 2012

(86) PCT No.: PCT/JP2012/001105
§ 371 (c)(1),
(2), (4) Date: Nov. 19, 2012

(87) PCT Pub. No.: WO2012/124260
PCT Pub. Date: Sep. 20, 2012

(30) Foreign Application Priority Data

Mar. 14, 2011 (JP) .................. 2011-055865

(51) Int. Cl.
*G06K 9/00* (2006.01)
(52) U.S. Cl.
USPC .......................... 382/147; 348/126
(58) Field of Classification Search .............. 382/106, 382/108, 141, 144, 145, 147, 150; 348/86, 348/87, 92, 126; 700/95, 96, 109, 110
See application file for complete search history.

(56) References Cited

U.S. PATENT DOCUMENTS

| | | | |
|---|---|---|---|
| 5,097,516 A | 3/1992 | Amir | |
| 5,495,337 A * | 2/1996 | Goshorn et al. | 356/601 |
| 5,862,973 A * | 1/1999 | Wasserman | 228/105 |
| 6,317,513 B2 * | 11/2001 | Michael et al. | 382/145 |
| 7,023,559 B1 * | 4/2006 | Coulombe et al. | 356/511 |
| 7,181,058 B2 * | 2/2007 | Weisgerber et al. | 382/145 |

(Continued)

FOREIGN PATENT DOCUMENTS

| | | |
|---|---|---|
| JP | 6-168321 | 6/1994 |
| JP | 10-311713 | 11/1998 |

(Continued)

OTHER PUBLICATIONS

International Search Report issued Mar. 27, 2012 in International (PCT) Application No. PCT/JP2012/001105.

*Primary Examiner* — Claire X Wang
*Assistant Examiner* — Shervin Nakhjavan
(74) *Attorney, Agent, or Firm* — Wenderoth, Lind & Ponack, LLP.

(57) ABSTRACT

A method of determining a solder paste height of solder paste printed on a circuit board, the method including obtaining a two-dimensional image of the circuit board which is captured from above a solder printed surface, and determining the solder paste height corresponding to a pixel value of each of pixels of the two-dimensional image, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model.

2 Claims, 6 Drawing Sheets

U.S. PATENT DOCUMENTS

| | | | |
|---|---|---|---|
| 2002/0191834 A1* | 12/2002 | Fishbaine | 382/150 |
| 2006/0079008 A1* | 4/2006 | Nishimaki et al. | 438/11 |
| 2009/0180679 A1* | 7/2009 | Hackney et al. | 382/141 |
| 2010/0007896 A1* | 1/2010 | Fishbaine | 356/603 |
| 2010/0260409 A1* | 10/2010 | Ben-Levy | 382/141 |
| 2010/0290696 A1* | 11/2010 | Jeong et al. | 382/147 |
| 2011/0002529 A1* | 1/2011 | Jeong et al. | 382/147 |
| 2011/0068473 A1* | 3/2011 | Lee et al. | 257/773 |

FOREIGN PATENT DOCUMENTS

| | | |
|---|---|---|
| JP | 2007-134406 | 5/2007 |
| JP | 2008-039750 | 2/2008 |
| JP | 2008-309580 | 12/2008 |
| JP | 2009-042089 | 2/2009 |
| JP | 2009-168453 | 7/2009 |
| JP | 2009-294115 | 12/2009 |

* cited by examiner

METHOD OF DETERMINING SOLDER PASTE HEIGHT AND DEVICE FOR DETERMINING SOLDER PASTE HEIGHT

TECHNICAL FIELD

The present invention relates to methods of determining a solder paste height of solder paste printed on a circuit board, and devices for determining a solder paste height of solder paste printed on a circuit board.

BACKGROUND ART

A mounted-board manufacturing system, which manufactures circuit boards on each of which components are mounted (hereinafter, referred to as "component mounted boards" or "mounted boards"), includes: a printer that prints solder paste on each circuit board; mounters that mounts components on the circuit board with printed solder paste; and a reflow machine that solders the mounted components. Target circuit boards are transported on a line of a conveyer in the mounted-board manufacturing system and manufactured as mounted boards in the conveyer system. More specifically, respective machines perform their processes for each circuit board. For example, for each circuit board, the printer prints solder paste on the circuit board, the mounter mounts various-sized numerous components on the circuit board, and then the reflow machine solders the components. Each of mounted boards is manufactured in a series of manufacturing processes performed by these machines. Such a mounted board manufactured in the above-described manner is eventually embedded in an end product such as a home appliance.

This mounted-board manufacturing system sometimes produces defective component mounted boards. From among various causes of poor quality, there is a defect in printing solder paste. For example, if a defect occurs in printing solder paste on a circuit board but subsequent processes are performed on the printed board, in more details, components are mounted and soldered on the circuit board, this results in various wastes in use of the mounted-board manufacturing system, consumption of the components, and the like.

To reduce the number of defective products and reduce waste processes in the mounted-board manufacturing system, it is effective to detect occurrence of a defect in an early stage and take measures when the defect occurs in the middle of a series of the manufacturing processes.

Conventionally, a technique has been proposed by which an inspection machine arranged for a process subsequent to a printing process inspects how a printer prints solder paste on each circuit board (see, Patent literature (PTL) 1 for example). In the technique as described in PTL 1, position, area, and others of the printed solder paste are measured using two-dimensional image captured by a camera with a solid-state image sensing device. In addition, a height of printed solder paste is also measured using a laser ranging unit.

Based on the position, area, and height of the solder paste measured in such a manner, the inspection machine can inspect how the printer prints solder paste on each circuit board.

CITATION LIST

Patent Literature

[PTL 1] Japanese Unexamined Patent Application Publication No. 2007-134406

SUMMARY OF INVENTION

Technical Problem

However, the measurement of the height of printed solder paste using the laser ranging unit, as described in PTL 1, has a problem that manufacturing cost of the inspection machine increases. In addition, the machines capable of installing the laser ranging unit are limited because the laser ranging unit is relatively heavy. The laser ranging unit also has the problem that it takes relatively long time to determine the solder paste height.

In view of this, the present invention was conceived in order to solve the above problems, and has an object to provide a method of determining the solder paste height and a device for determining the solder paste height, which can determine the height of printed solder paste in a rather straightforward manner without using the laser ranging unit.

Solution to Problem

In order to achieve the object, a method of determining a solder paste height according to an aspect of the present invention includes: obtaining a two-dimensional image of the circuit board which is captured from above a solder printed surface; and determining the solder paste height corresponding to a pixel value of each of pixels of the two-dimensional image, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model With this, the solder paste height corresponding to a pixel value of each of pixels of the two-dimensional image can be determined, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model. More specifically, without using a laser ranging unit, the solder paste height can be determined in a straightforward manner using a two-dimensional image.

In addition, it is preferable that the height information include a proportionality coefficient between an intensity value in the HSI color model and the solder paste height, and, in the determining, the solder paste height is determined by multiplying the intensity value by the proportionality coefficient included in the height information.

With this, the solder paste height can be determined easily by using a proportional relationship between the solder paste height and the intensity value in the HSI color model.

In addition, it is preferable that the height information include a proportionality coefficient between a luminance value of blue in the RGB color model and the solder paste height, and, in the determining, the solder paste height is determined by multiplying the luminance value of blue by the proportionality coefficient included in the height information.

With this, the solder paste height can be determined easily by using a proportional relationship between the solder paste height and the luminance value of blue. A two-dimensional image generated by a general imaging device is an image represented using the RGB color model. Therefore, this method does not necessitate converting the two-dimensional image represented using the RGB color model, which is obtained from the imaging device, to a two-dimensional image represented using the HSI color model, thus reducing a processing load.

In addition, it is preferable that the height information show that a difference between an intensity value and a hue value in the HSI color model corresponds to the solder paste height, and, in the determining, the solder paste height is determined by calculating the difference.

With this, the solder paste height can be determined by using the correspondence of the solder paste height to the difference between the intensity value and the hue value. As a result, regardless of the type of circuit board, the solder paste height can be determined generally.

In addition, it is preferable that the method further include displaying the determined solder paste height.

With this, the heights of solder paste can be displayed for an inspector to visually inspect how the solder paste is printed on each circuit board.

In addition, a device for determining the solder paste height according to an aspect of the present invention includes: an image obtaining unit which obtains a two-dimensional image of the circuit board which is captured from above a solder printed surface; and a height determining unit which determines the solder paste height corresponding to a pixel value of each of pixels of the two-dimensional image, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model.

With this structure, such a device has an advantageous effect similar to the above method.

Advantageous Effects of Invention

According to this present invention, heights of solder paste printed on a circuit board can be determined in a rather straightforward manner without using a laser ranging unit.

DESCRIPTION OF EMBODIMENT

In some experiments, inventors of this application found that a pixel value in a two-dimensional image generated by capturing a circuit board with printed solder paste (i.e. a value represented using the RGB color model or the HSI color model) depends on a solder paste height. The following paragraphs will describe an embodiment according to the present invention in which dependency between the pixel value of the two-dimensional image and the solder paste height is utilized to determine the solder paste height based on the two-dimensional image.

Note that the embodiment described below is a preferable, specific example of the present invention. The numerical values, shapes, constituent elements, the arrangement and connection of the constituent elements, steps, the processing order of the steps etc. shown in the following embodiment is a mere example, and thus do not limit the present invention. Thus, among the constituent elements in the following embodiment, constituent elements not recited in any of the independent claims indicating the most generic concept of the present invention are described as preferable constituent elements.

Embodiment

A device for determining a solder paste height 130 according to an embodiment of the present invention determines a solder paste height corresponding to a pixel value of each of pixels of a two-dimensional image, based on height information which defines a relationship between the pixel value and the solder paste height. Hereinafter, the embodiment will be described with reference to drawings.

Figure 1:
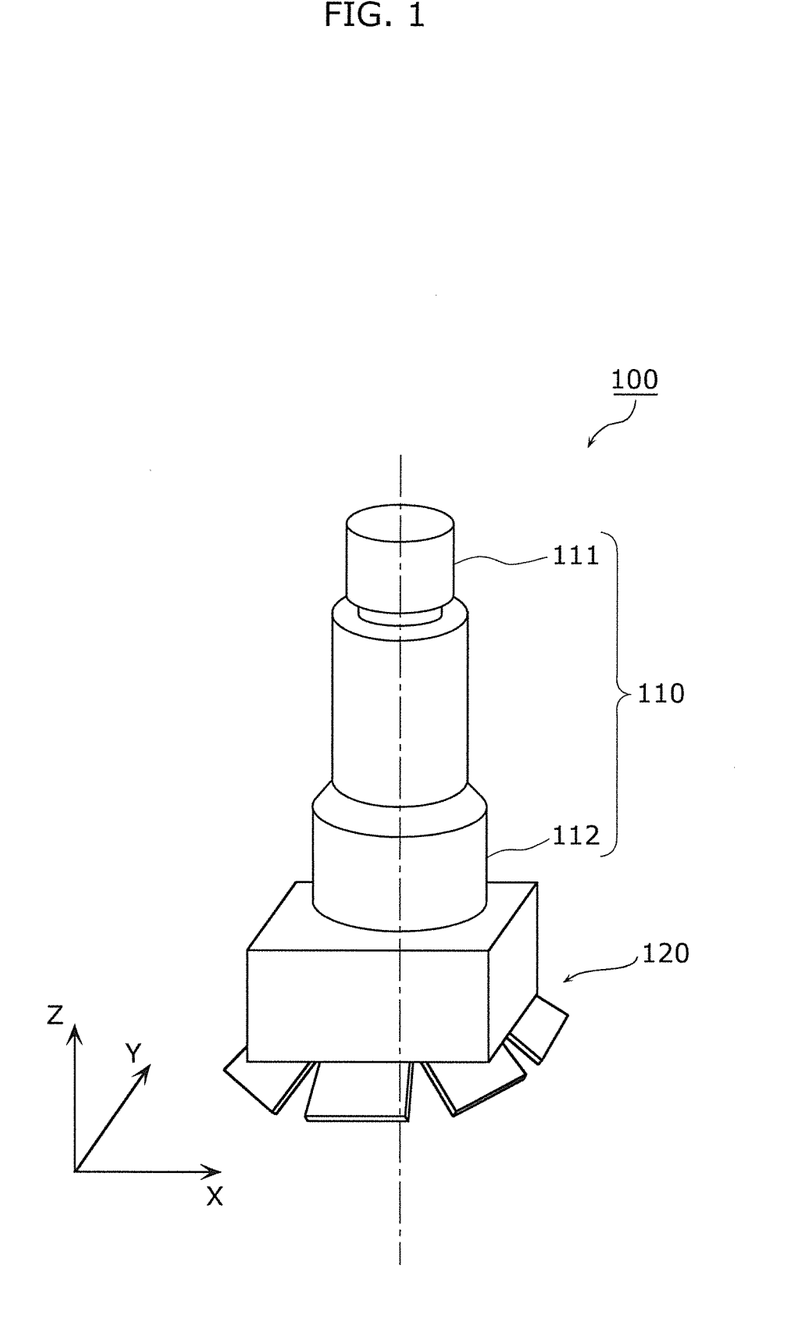
FIG. 1 illustrates an outline view of an inspection machine according to an embodiment of the present invention.
Figure 2A:
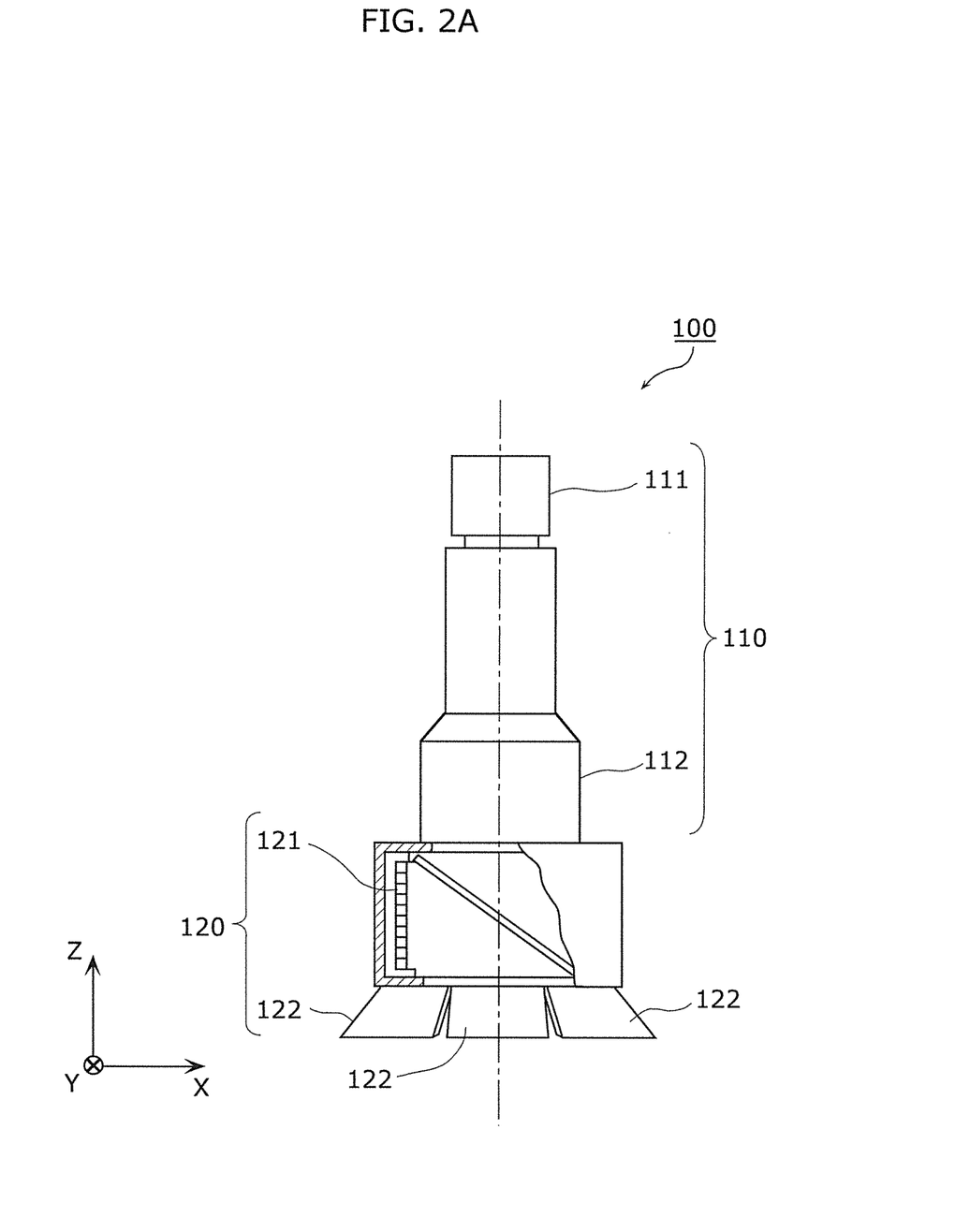
FIG. 2A illustrates an elevation view of the inspection machine according to the embodiment of the present invention.
Figure 2B:
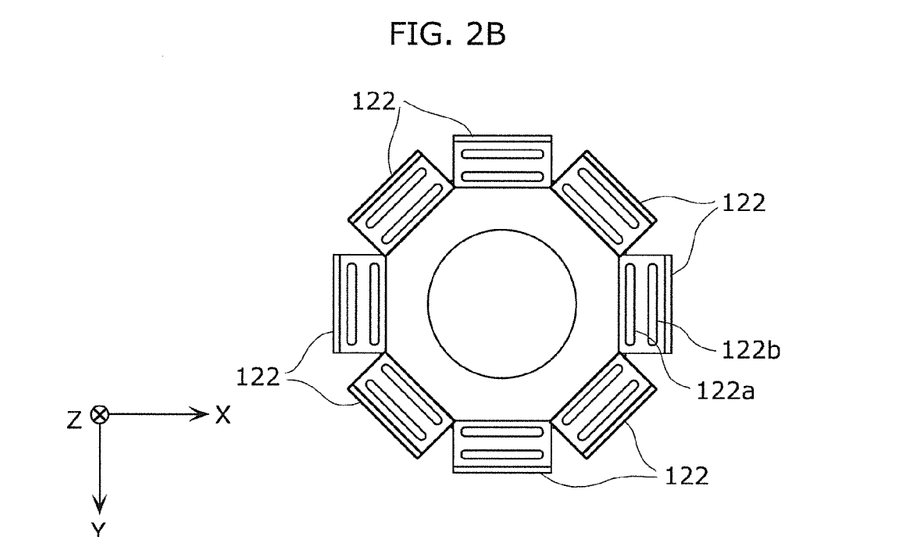
FIG. 2B illustrates a bottom view of the inspection machine according to the embodiment of the present invention.
Figure 3:
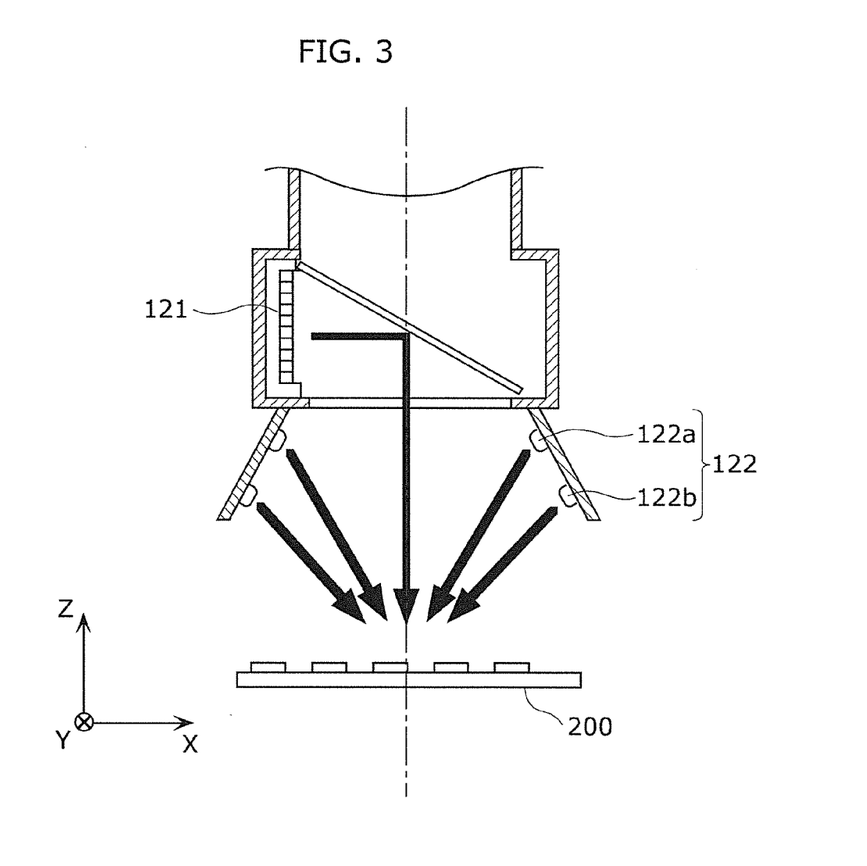
FIG. 3 illustrates a cross-sectional view to describe a lighting device included in the inspection machine according to the embodiment of the present invention.
Figure 4:
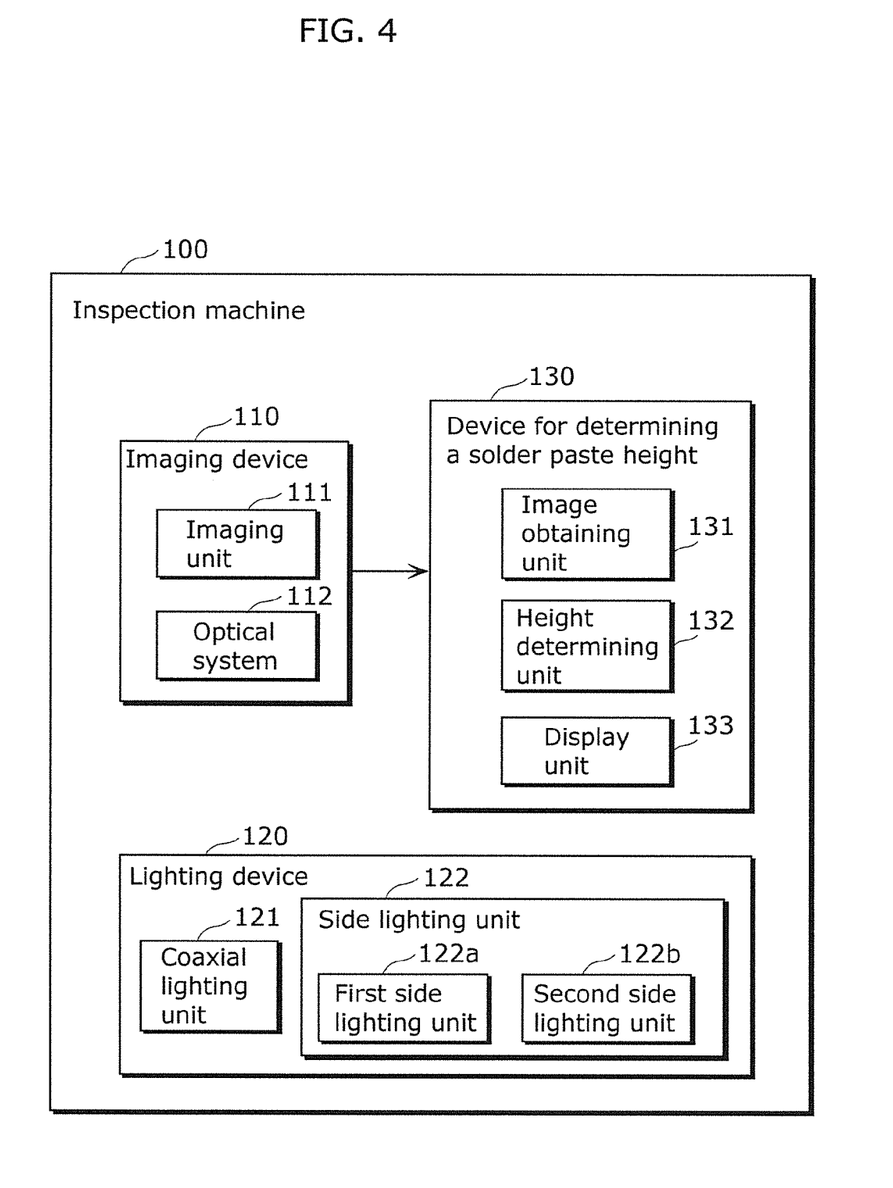
FIG. 4 illustrates a block diagram showing a functional structure of the inspection machine according to the embodiment of the present invention.

FIG. 1 illustrates an outline view of an inspection machine according to the embodiment of the present invention. FIG. 2A illustrates an elevation view (partial cross-sectional view) of the inspection machine according to the embodiment of the present invention. FIG. 2B illustrates a bottom view of the inspection machine as shown in FIG. 2A, where the inspection machine is depicted from the bottom in a direction of Z-axis. FIG. 3 illustrates a cross-sectional view to describe a lighting device according to the embodiment of the present invention. FIG. 4 illustrates a block diagram showing a functional structure of the inspection machine according to the embodiment of the present invention. Note that, in the above drawings, a solder printed surface of the circuit board is parallel to X-Y plane, and the Z-axis corresponds to the solder paste height.

As shown in FIG. 1 to FIG. 4, the inspection machine 100 includes an imaging device 110, a lighting device 120, and the device for determining the solder paste height 130.

The imaging device 110 captures a circuit board 200 with printed solder paste to generate the two-dimensional image. In the embodiment, the imaging device 110 generates the two-dimensional image represented using the RGB (Red, Green, Blue) color model. More specifically, the imaging device 110 includes an imaging sensor 111 and an optical system 112 as shown in FIG. 1 and FIG. 2.

The imaging sensor 111 is a solid-state image sensing device such as a charge coupled device (CCD) imaging sensor or a complementary metal oxide semiconductor (CMOS) imaging sensor. In the embodiment, for the imaging sensor 111, the CCD imaging sensor is used which converts light that has passed through the optical system 112 to respective electric signals of the RGB components. The imaging sensor 111 generates the two-dimensional image represented using the RGB color model, which comprises more than 1 million pixels for example.

The optical system 112 includes lens which collects light reflected from the circuit board 200 in the imaging area of the imaging sensor 111. Note that an optical axis of the optical system 112 is depicted as dashed line.

The lighting device 120 emits light to the circuit board 200. The lighting device 120 includes a coaxial lighting unit 121 and a side lighting unit 122.

The coaxial lighting unit 121 is a light source which is located above the circuit board 200 and emits light downward to it. More specifically, the coaxial lighting unit 121 emits light to a point on top surface of the circuit board 200 where the optical axis of the optical system 112 and the circuit board 200 intersect, in a direction of about 90 degrees from the surface of the circuit board 200 (in a direction of Z-axis). In the embodiment, the coaxial lighting unit 121 has a light-emitting diode (LED) that emits white light and a LED that emits red light. The LED that emits white light and the LED that emits red light are arranged alternately.

The side lighting unit 122 arranged in a circular pattern is a light source which is located lateral to the circuit board 200 and emits light obliquely downward to it. In the embodiment, the side lighting unit 122 includes a first side lighting unit 122a and a second side lighting unit 122b.

The first side lighting unit 122a is arranged above the second side lighting unit 122b and emits light obliquely downward to the circuit board 200. In the embodiment, a LED that emits white light is used as the first side lighting unit 122a. In this case, as shown in FIG. 3, the first side lighting unit 122a emits light to the point where the optical axis of the optical system 112 and the circuit board 200 intersect, in a direction of about 50 degrees from the surface of the circuit board 200 for example.

The second side lighting unit 122b is arranged below the first side lighting unit 122a and emits light obliquely downward to the circuit board 200. In the embodiment, a LED that emits white light is used as the second side lighting unit 122b. In this case, as shown in FIG. 3, the second side lighting unit 122b emits light to the point where the optical axis of the optical system 112 and the circuit board 200 intersect, in a direction of about 35 degrees from the surface of the circuit board 200 for example.

Thus, in the side lighting unit 122, each of the first side lighting unit 122a and the second side lighting unit 122b emits light to the circuit board 200 at a different angle to avoid making a shadow on the solder printed surface of the circuit board 200.

The following paragraphs will describe the device for determining the solder paste height 130 with reference to FIG. 4.

The device for determining the solder paste height 130 can be implemented as a processor, a memory, and the like, and determines the solder paste height of solder paste printed on the circuit board 200 based on the two-dimensional image captured by the imaging device 110. As shown in FIG. 4, the device for determining the solder paste height 130 includes an image obtaining unit 131 and a height determining unit 132.

The image obtaining unit 131 obtains the two-dimensional image of the circuit board 200. More specifically, the image obtaining unit 131 obtains the two-dimensional image of the circuit board 200 which is captured from above the solder printed surface.

In the embodiment, the image obtaining unit 131 obtains the two-dimensional image represented using the RGB color model from the imaging device 110. Subsequently, the image obtaining unit 131 converts the two-dimensional image represented using the RGB color model (hereinafter referred to as a "RGB image") to a two-dimensional image represented using the Hue, Saturation, and Intensity (HSI) color model (hereinafter referred to as a "HSI image").

The height determining unit 132 determines the solder paste height corresponding to the pixel value of each of pixels of the two-dimensional image, based on the height information which defines the relationship between the solder paste height and the pixel value that is a value representing at least one of luminance of red in the RGB color model, luminance of green in the RGB color model, luminance of blue in the RGB color model, hue in the HSI color model, saturation in the HSI color model, and intensity in the HSI color model. In the embodiment, the height information shows that the solder paste height is proportional to the pixel value, and contains a proportionality coefficient between the solder paste height and the pixel value (for example "0.5"). More specifically, the height determining unit 132 determines the solder paste height by multiplying an intensity value by the proportionality coefficient between the intensity value and the solder paste height.

Note that the height information need not contain the proportionality coefficient. For example, the height information may be created in table form which stores the solder paste height in association with the pixel value.

In addition, it is preferable that the height information be stored for each type of circuit board 200 and each type of land processing which is performed on conductor pattern surface that is a captured surface of the circuit board 200. For example, it is preferable to separately store height information sets such as when copper is used in land processing of a glass epoxy board, when gold is used in land processing of a glass epoxy board, and when copper is used in land processing of a polyimide board. With this, the device for determining the solder paste height 130 can appropriately determine the solder paste height according to the type of circuit board or land processing. Note that the land processing includes a processing where no surface treatment is performed on land material.

A display unit 133 such as a liquid crystal display panel displays the determined heights. More specifically, the display unit 133 displays, as a three-dimensional chart, the height for each of the pixels included in the two-dimensional image.

A glass epoxy board, a polyimide board, flexible board, ceramic board, or the like is used as the circuit board 200.

The following paragraphs will describe various operations in the above-mentioned inspection machine 100.

Figure 5:
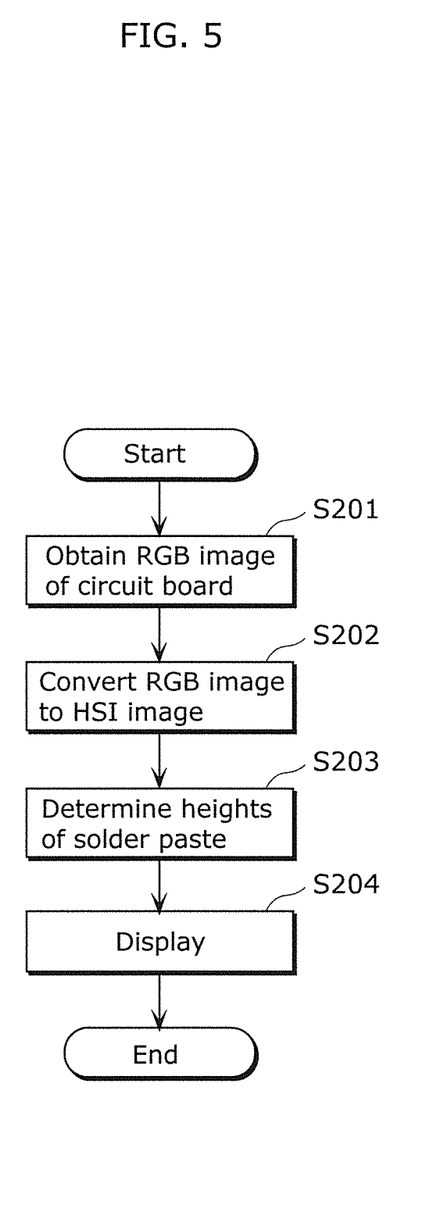
FIG. 5 illustrates a flowchart showing a method of determining a solder paste height according to the embodiment of the present invention.

FIG. 5 illustrates a flowchart showing a method of determining a solder paste height according to the embodiment of the present invention. Note that, in the following method of determining the solder paste height, height information appropriate to the circuit board 200 is created and stored in advance.

The image obtaining unit 131 obtains the two-dimensional image of the circuit board 200 (S201). In the embodiment, the image obtaining unit 131 obtains the two-dimensional image represented using the RGB color model (the RGB image) from the imaging device 110. Then, the height determining unit 132 converts the RGB image into a HSI image (S202).

Subsequently, for each pixel of the captured two-dimensional image (the RGB image, the HSI image, and so on), the height determining unit 132 determines a solder paste height corresponding to a pixel value of the pixel based on height information which defines a relationship between the pixel value (the RGB color model, the HSI color model) and the solder paste height (S203). In the embodiment, the height information shows that the solder paste height is proportional to an intensity value in the HSI image. For example, when the height information contains a proportionality coefficient 0.5 and intensity value of a pixel included in the HSI image is 225, the height determining unit 132 determines that the solder paste height in the pixel is 112.5 μM (solder paste height=intensity value×proportionality coefficient).

Figure 6:
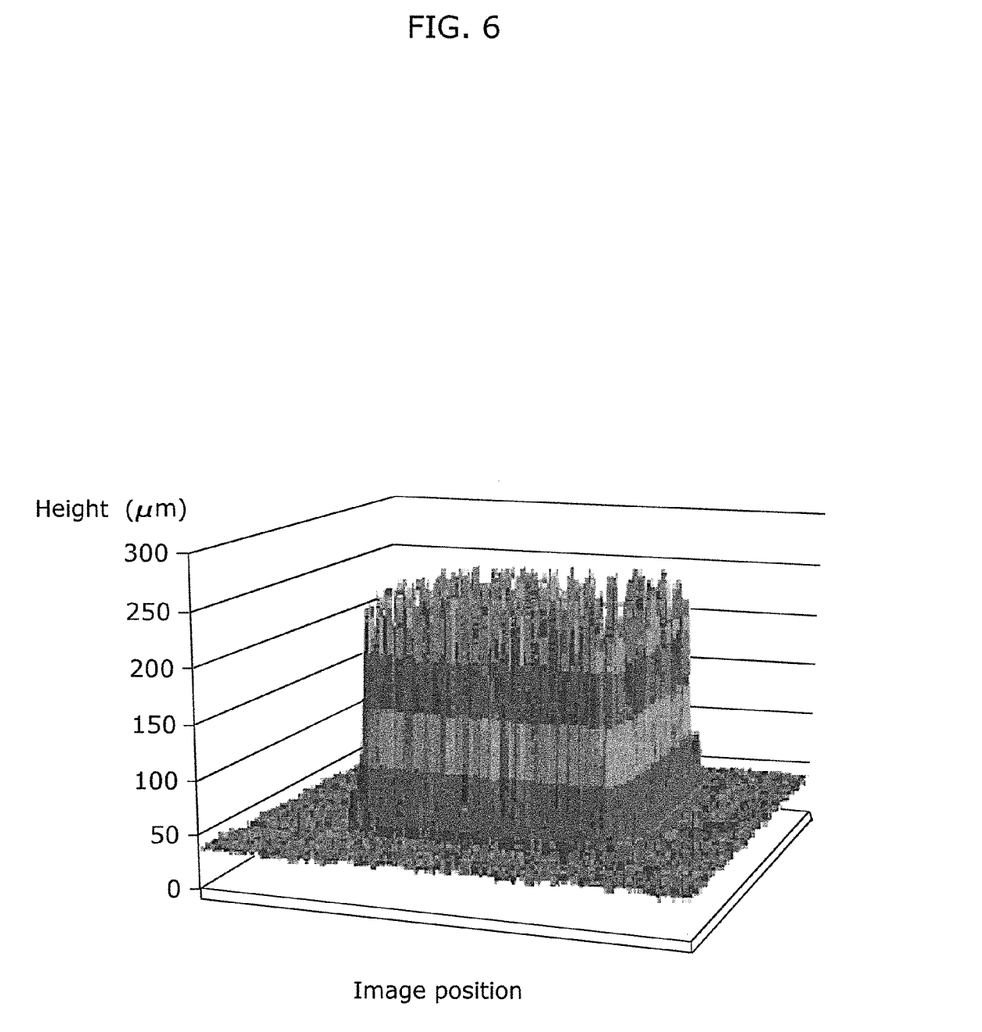
FIG. 6 illustrates an exemplary display of the solder paste height according to the embodiment of the present invention.

The display unit 133 displays the solder paste height determined in such a manner (S204). For example, as shown in FIG. 6, the display unit 133 displays the solder paste height in each pixel position as a three-dimensional chart. With this, an inspector can easily check how the solder paste is printed on each circuit board 200 by looking at the three-dimensional chart displayed on the display unit 133.

Note that the height information can be created by measuring the solder paste height and the intensity value in the HSI image generated by capturing the board with solder paste having a known height. An exemplary process of creating such height information will be described below.

First, the circuit board 200 with printed solder paste having a predetermined height is captured by the imaging device 110. Subsequently, the captured RGB image is converted into the HSI image. In the converted HSI image, an intensity value of a pixel corresponding to a position where the solder paste is printed is detected. A proportion of the solder paste height of solder paste printed on the circuit board 200 (the predetermined height) to the intensity value detected above is calculated as the proportionality coefficient.

As described above, the proportionality coefficient between the intensity value and the solder paste height is calculated. Note that it is preferable to adjust the light of the lighting device 120 so as to saturate the intensity value corresponding to an upper limit for the solder paste height to be determined (for example, 255 for 256 grayscales). With this, the solder paste height can be determined more precisely.

It is also preferable to capture a reference board (for example, a matte black circuit board) in the light of the lighting device 120 adjusted above in order to calculate the hue, saturation and intensity values in the HSI image as reference values (for example, H(50/255), S(50/255) and I(100/255)). With this, when the lighting device 120 is adjusted so as to match a value of the HSI image obtained as a result of capturing the reference board to the reference value (for example, the first side lighting unit (20/255), the second side lighting unit (200/255)), the process does not necessitate the recalculation of the proportionality coefficient using the circuit board with printed solder paste.

As described above, the inspection machine 100 according to the embodiment can determine the solder paste height corresponding to the pixel value of each pixel of the two-dimensional image, based on the height information which defines the relationship between the pixel value and the solder paste height. In other words, without using the laser ranging unit, the solder paste height can be determined in the straightforward manner using the two-dimensional image. More specifically, the solder paste height can be determined easily by using the proportional relationship between the solder paste height and the intensity value in the HSI image.

[Variation 1]

The following paragraphs will describe a variation 1 of the present invention.

In the above-mentioned embodiment, intensity value in an HSI image is used to determine a solder paste height, whereas, in the variation 1, a luminance value of blue in a RGB image is used to determine the solder paste height.

More specifically, the height determining unit 132 according to the variation 1 determines the solder paste height by multiplying the luminance value of blue by the proportionality coefficient between the luminance value of blue and the solder paste height, which is contained in height information.

Among the luminance values of red, green, and blue in the RGB image, the luminance value of blue is the closest to the intensity value in the HSI image. Thus, the height determining unit 132 can also determine the solder paste height using the luminance value of blue in the RGB image as described in the variation 1.

Therefore, since the solder paste height can be determined using the luminance value of blue, the device for determining the solder paste height 130 does not necessitate converting the RGB image to the HSI image (S202), thus reducing a processing load.

[Variation 2]

The following paragraphs will describe a variation 2 of the present invention.

In the above-mentioned embodiment, among hue, saturation, and intensity values in an HSI image, only the intensity value is used to determine a solder paste height, whereas, in the variation 2, a difference between the intensity value and the hue value is used to determine the solder paste height.

In other words, the height determining unit 132 according to the variation 2 determines the solder paste height by subtracting the hue value from the intensity value in the HSI image. More specifically, assuming that the intensity value and the hue value is 225 and 112, respectively, the height determining unit 132 determines that the solder paste height is 113 μm (solder paste height=intensity value−hue value).

The difference between the intensity value and the hue value corresponds to the solder paste height because the hue value corresponds to a height of a virtual resist surface (a surface of the circuit board 200 (a reference surface of height)). This virtual resist surface corresponds the green solder-resist surface for protecting a surface (green resist surface) when the glass epoxy board (so-called "printed circuit board") is used as a circuit board 200 for example. Therefore, when a color of the reference surface of height which is the surface of the circuit board 200 differs from a color of a measured surface, a use of the difference between the intensity value and the hue value allows the height determining unit to determine the solder paste height regardless of the type of circuit board, thus expanding the versatility.

Note that, when there is little difference in color between the reference surface of height and a surface to be measured, another reference surface of height having a color vastly different from the color of the surface to be measured may be provided inside or outside the circuit board to measure the solder paste height.

The height determining unit 132 determines the solder paste height by subtracting the hue value from the intensity value in the HSI image, but the solder paste height may be also further determined using a correction value such as a proportionality coefficient in order to determine the solder paste height more precisely.

Thus, the device for determining the solder paste height 130 according to an aspect of the present invention has been described based on the embodiment, but the present invention is not limited to this embodiment. Various modifications to the present embodiment that can be conceived by those skilled in the art, and forms configured by combining constituent elements in different embodiments without departing from the teachings of the present invention are included in the scope of the present invention.

For example, in the above embodiment, the device for determining the solder paste height 130 includes the display unit 133, but it need not be included. More specifically, the method of determining the solder paste height as shown in FIG. 5 need not include Step S204. In this case, the device for determining the solder paste height 130 can provide information indicating the determined height (value, graph of height, and the like) to a display device for example.

The device for determining the solder paste height 130 may also further determine an area in which solder paste is printed on the circuit board 200, based on the two-dimensional image. Then, the device for determining the solder paste height 130 may determine an amount of solder paste based on the determined area and the determined height. With this, an inspector can inspect more precisely how the solder paste is printed on each circuit board.

Furthermore, the imaging device 110 may capture a solder printed surface of the circuit board 200 by scanning relatively because the imaging device need not capture the whole solder printed surface at one time. More specifically, the imaging device 110 may include a line imaging sensor as the imaging sensor 111 instead of an area imaging sensor which need not be included as the imaging sensor 111.

In addition, the inspection machine 100 may determine whether or not the determined solder paste height is within the predetermined range of heights in order to inspect how the solder paste is printed on the circuit board 200. The inspection machine 100 may also provide a warning alarm or turn on an alert lamp when the inspection is not passed for example. Thus, this reduces an inspector's burden.

In addition, the device for determining the solder paste height 130 may be provided outside the inspection machine 100 because it need not include the device for determining the solder paste height. Furthermore, the inspection machine 100 may be included in a mounter or a printer.

In addition, a part or all of the constituent elements included in the device for determining the solder paste height 130 according to the embodiment may be configured of one system large scale integration (LSI). For example, the device for determining the solder paste height 130 may be configured of a system LSI having the image obtaining unit 131 and the height determining unit 132.

The system LSI is a super multi-function LSI that is manufactured by integrating plural components in one chip, and is specifically a computer system which is configured by including a microprocessor, a ROM, a RAM, and so on. A computer program is stored in the RAM. The system LSI accomplishes its functions through the operation of the microprocessor in accordance with the computer program.

The name used here is a system LSI, however, it may also be referred to as an IC, an LSI, a super LSI, or an ultra LSI in accordance with the degree of integration. Furthermore, the integration may be achieved, not only as LSI, but also as a dedicated circuit or a general purpose processor. Field Programmable Gate Array (FPGA) that can be programmed after manufacturing LSI or reconfigurable processor that can re-configure the connection and setting of the circuit sell inside the LSI may be used.

Furthermore, when integration circuit technology replacing LSI emerges with the advancement of semiconductor technology or other derivative technology, the technology may be used naturally for integrating functional block. Possibility includes application of biotechnology.

It should be noted that the present invention can be implemented, not only as a device for determining a solder paste height which includes such distinctive processing units, but also as a method of determining a solder paste height which has, as steps, the distinctive processing units included in the device for determining the solder paste height. The present invention can also be implemented as a program which causes a computer to execute each of the distinctive steps included in the method of determining the solder paste height. Needless to say, such a program can be distributed via a non-transitory computer-readable recording medium such as a Compact Disc Read Only Memory (CD-ROM) or via a communication network such as the Internet.

INDUSTRIAL APPLICABILITY

The present invention is applicable to a device for determining a solder past height of solder past printed on the circuit board and an inspecting machine for inspecting how the solder paste is printed on each circuit board prior to mounting components on each circuit board.

REFERENCE SIGNS LIST

100 Inspection machine
110 Imaging device
111 Imaging sensor
112 Optical system
120 Lighting device
121 Coaxial lighting unit
122 Side lighting unit
122a First side lighting unit
122b Second side lighting unit
130 Device for determining a solder paste height
131 Image obtaining unit
132 Height determining unit
133 Display unit
200 Circuit board

The invention claimed is:

1. A method of determining a solder paste height of solder paste printed on a circuit board, the method comprising:
   obtaining a two-dimensional image of the circuit board which is captured from above a solder printed surface; and
   determining the solder paste height corresponding to a pixel value of each of pixels of the two-dimensional image, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model,
   wherein the height information shows that a difference between an intensity value and a hue value in the HSI color model corresponds to the solder paste height, and
   in the determining, the solder paste height is determined by calculating the difference.

2. A device for determining a solder paste height printed on a circuit board, the device comprising:
   an image obtaining unit configured to obtain a two-dimensional image of the circuit board which is captured from above a solder printed surface; and
   a height determining unit configured to determine the solder paste height corresponding to a pixel value of each of pixels of the two-dimensional image, based on height information which defines a relationship between the pixel value and the solder paste height, the pixel value being a value representing at least one of luminance of red in a RGB color model, luminance of green in the RGB color model, luminance of blue in the RGB color model, hue in a HSI color model, saturation in the HSI color model, and intensity in the HSI color model,
   wherein the height information shows that a difference between an intensity value and a hue value in the HSI color model corresponds to the solder paste height, and the height determining unit determines the solder paste height by calculating the difference.

\* \* \* \* \*